(12) United States Patent
Al-Saffar

(10) Patent No.: US 9,155,594 B1
(45) Date of Patent: Oct. 13, 2015

(54) DENTAL EXTRACTOR

(71) Applicant: Abdulreidha A. J. A. Al-Saffar, Mubarak Al-Kabir (KW)

(72) Inventor: Abdulreidha A. J. A. Al-Saffar, Mubarak Al-Kabir (KW)

( * ) Notice: Subject to any disclaimer, the term of this patent is extended or adjusted under 35 U.S.C. 154(b) by 0 days.

(21) Appl. No.: 14/541,098

(22) Filed: Nov. 13, 2014

(51) Int. Cl.
*A61C 3/00* (2006.01)
*A61C 3/14* (2006.01)

(52) U.S. Cl.
CPC .................................. *A61C 3/14* (2013.01)

(58) Field of Classification Search
CPC ............ A61C 3/14; A61C 3/16; A61C 3/168; A61C 5/026; A61D 5/00
USPC .............................................. 433/49–79, 153
See application file for complete search history.

(56) References Cited

U.S. PATENT DOCUMENTS

| | | | |
|---|---|---|---|
| 1,666,860 A * | 4/1928 | Maranda | 433/161 |
| 1,702,487 A * | 2/1929 | Vasko | 433/25 |
| 2,027,470 A * | 1/1936 | Caruso | 433/158 |
| 2,777,198 A * | 1/1957 | Wallace | 433/118 |
| 5,478,350 A | 12/1995 | Kratsch et al. | |
| 5,575,646 A * | 11/1996 | Giannella | 433/76 |
| 5,620,459 A | 4/1997 | Lichtman | |
| 5,669,875 A * | 9/1997 | van Eerdenburg | 604/22 |
| 5,908,437 A * | 6/1999 | Asano et al. | 606/205 |
| 6,613,068 B2 * | 9/2003 | Ouchi | 606/205 |
| 2004/0209224 A1 | 10/2004 | Heasley | |
| 2005/0008987 A1 * | 1/2005 | Standish | 433/153 |

* cited by examiner

*Primary Examiner* — Cris L Rodriguez
*Assistant Examiner* — Matthew Saunders
(74) *Attorney, Agent, or Firm* — Richard C Litman

(57) ABSTRACT

The dental extractor includes a housing coupled to a flexible shaft having a proximal end, a distal end, and a lumen extending therethrough; a dental bridge coupled to the flexible shaft, the dental bridge having a top portion coupled to a first elongated member, including a first bottom support member, and a second elongated member, including a second bottom support member; an opening between the first bottom support member and the second bottom support member adapted to receive the tooth; a gripping mechanism having a top portion pivotally coupled to a first gripping member and a second gripping member, the gripping mechanism being slidably positioned between the first elongated member and the second elongated member of the dental bridge; a control mechanism positioned inside the housing to control the opening and closing of the gripping mechanism; and a selectively movable member coupled to the housing.

14 Claims, 8 Drawing Sheets

DENTAL EXTRACTOR

BACKGROUND OF THE INVENTION

1. Field of the Invention

The present invention generally relates to dental instruments, and more particularly to a dental extractor that reduces the chance of injury during the extraction of a tooth.

2. Description of the Related Art

Dental extraction procedures are uncomfortable and, at times, painful experiences. Typically, dentists rely on the use of dental pliers to grasp the crown region of the tooth to extract an unwanted or damaged tooth. To remove a tooth using a dental plier, the dentist must grab the crown region of the tooth and move the tooth back-and-forth and from side-to-side in order to loosen the root portion of the tooth from the gums so that it can be removed. By moving the tooth in these various directions, the dentist risks injuring the patient's lips, gums, and possibly even the surrounding teeth, not only causing the patient to suffer pain and discomfort, but also potentially causing further unnecessary damage to the surrounding teeth.

Thus, a dental extractor solving the aforementioned problems is desired.

SUMMARY OF THE INVENTION

The dental extractor includes a housing coupled to a flexible shaft having a proximal end, a distal end, and a lumen extending therethrough; a dental bridge coupled to the flexible shaft, the dental bridge having a top portion coupled to a first elongated member, including a first bottom support member, and a second elongated member, including a second bottom support member; an opening between the first bottom support member and the second bottom support member adapted to receive the tooth; a gripping mechanism having a top portion pivotally coupled to a first gripping member and a second gripping member, the gripping mechanism being slidably positioned between the first elongated member and the second elongated member of the dental bridge; a control mechanism positioned inside the housing, the control mechanism being configured to control the opening and closing of the gripping mechanism; and a selectively movable member coupled to the housing, the selectively movable member being configured to control the position of the gripping mechanism in relation to the tooth that is to be extracted. The dental bridge is inserted into the patient's mouth to support the upper jaw and the lower jaw, and the opening of the dental bridge is positioned over the tooth to be extracted to allow the dentist to grab the tooth using the gripping mechanism and to remove the tooth by pulling it upward in a linear direction. The dental extractor may include a coupling member coupled to a support member having at least one leg configured for attachment onto a dental chair.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
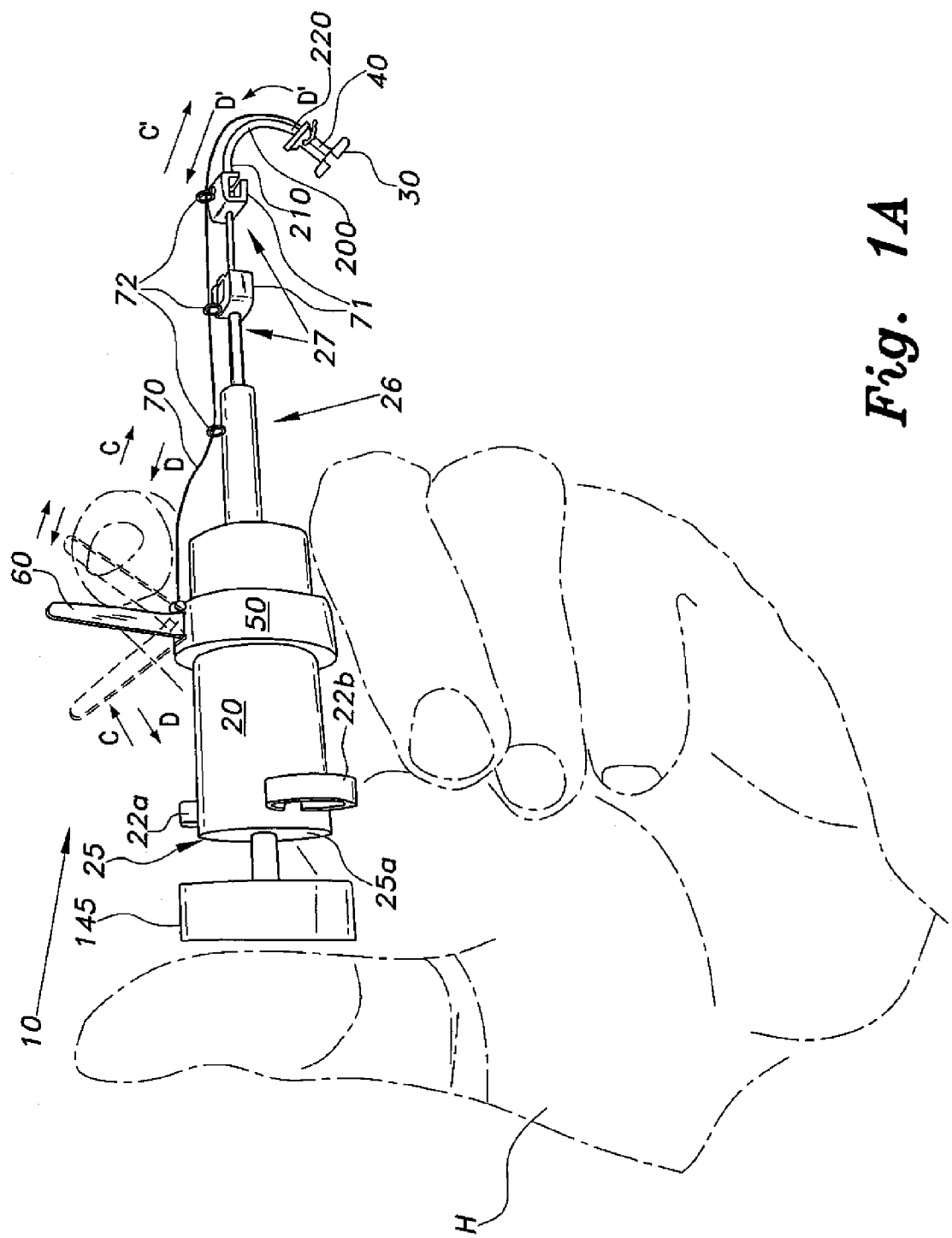
FIG. 1A is an environmental perspective view of a dental extractor according to the present invention.
Figure 1B:
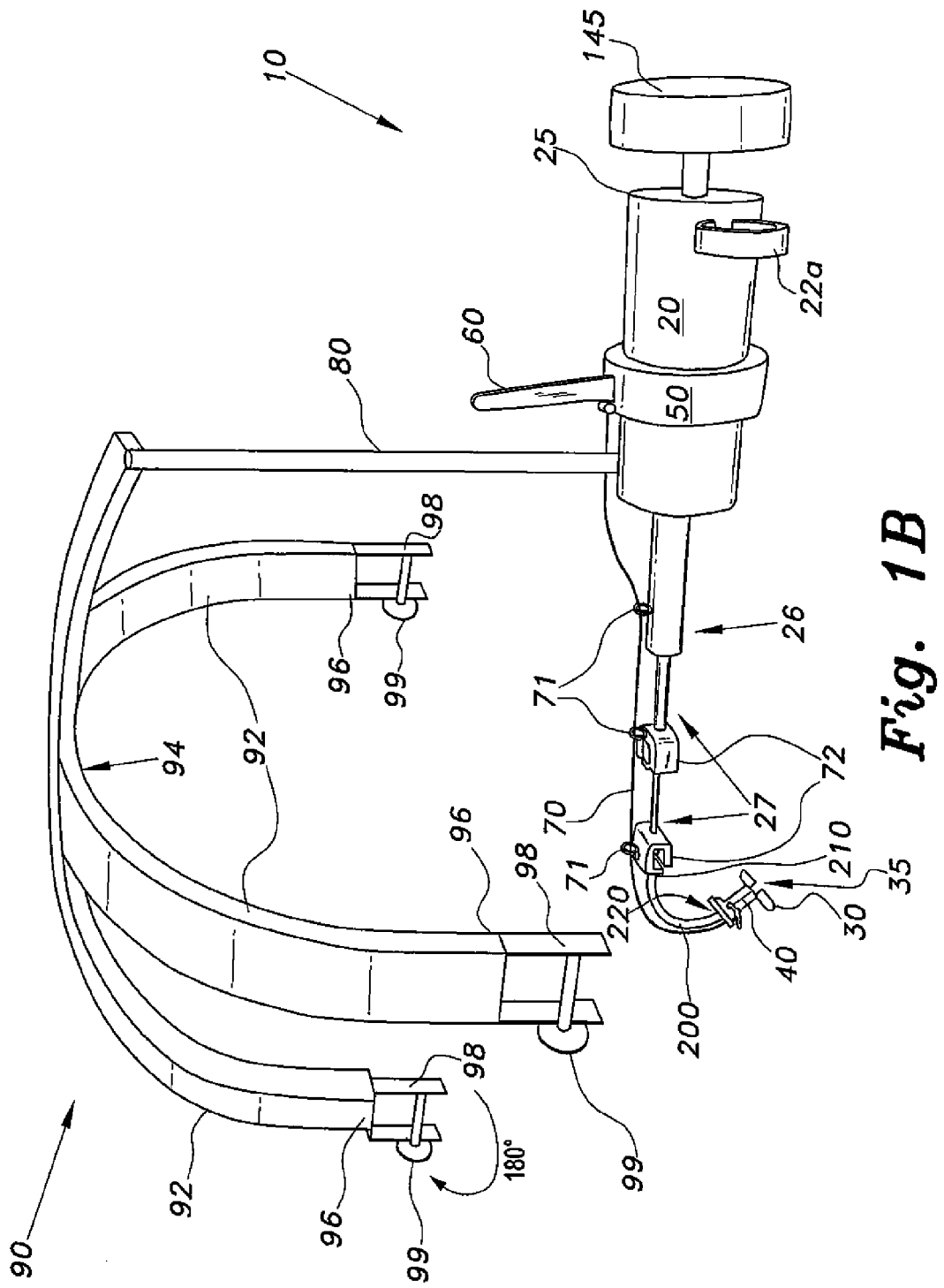
FIG. 1B is a perspective view of the dental extractor of FIG. 1 equipped with an optional support member.
Figure 2:
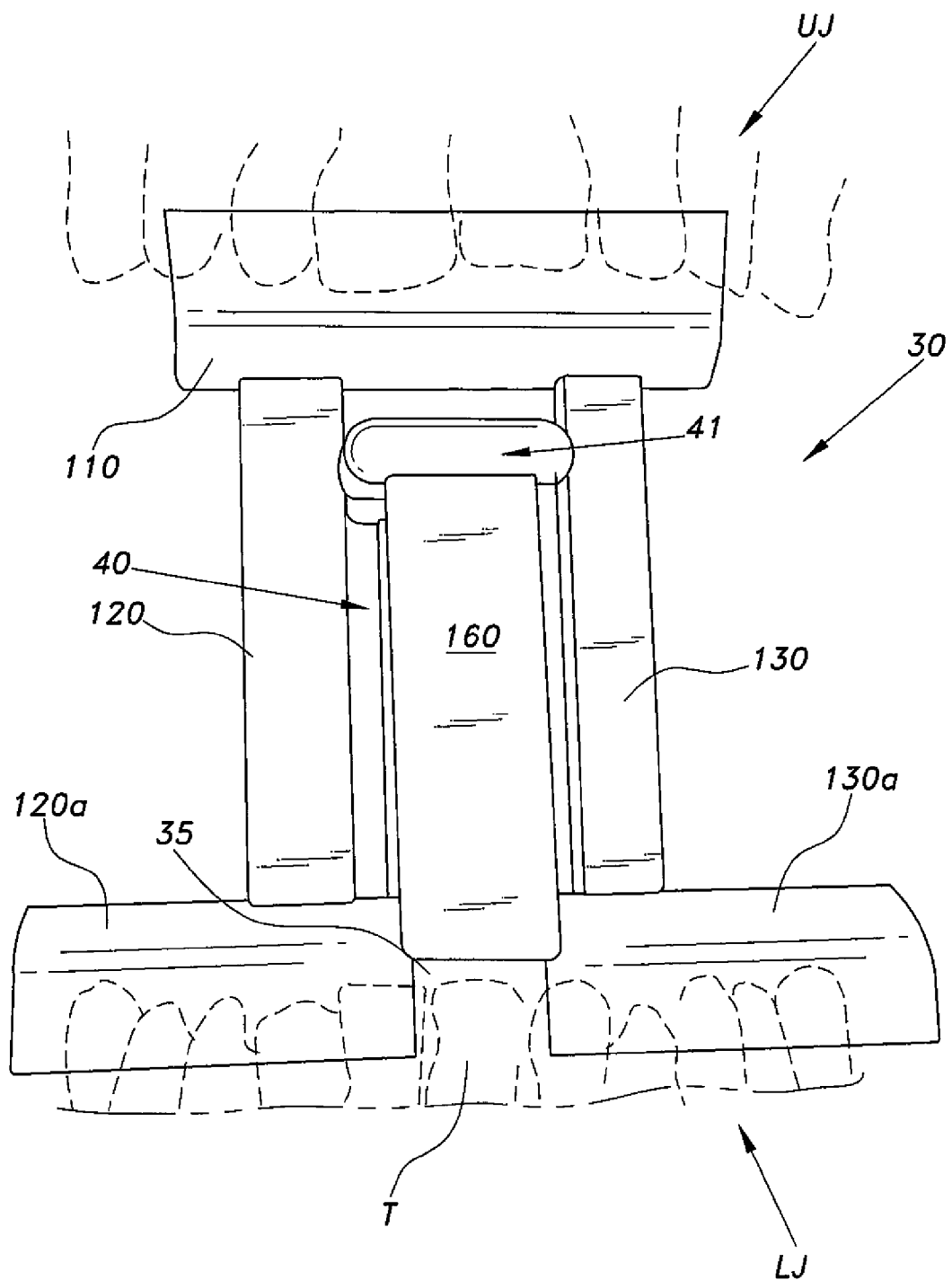
FIG. 2 is a front view of the dental bridge of the dental extractor of FIG. 1A, shown supporting the upper and lower jaw of a patient, the gripping mechanism being shown in the foreground.

Referring to FIGS. 1A-6, the dental extractor 10 includes a housing 20 coupled to a flexible shaft 200 having a proximal end 210, a distal end 220, and a lumen extending therethrough; a dental bridge 30 coupled to the flexible shaft 200, the dental bridge 30 (shown most clearly in FIG. 2) having a top portion 110 coupled to a first elongated member 120 including a first bottom support member 120a, and a second elongated member 130 including a second bottom support member 130a; an opening 35 between the first bottom support member 120a and the second bottom support member 130a adapted to receive the tooth T; a gripping mechanism 40 (shown most clearly in FIGS. 4A and 4B) having a top portion 41 pivotally coupling a first gripping member (jaw) 160 to a second gripping member (jaw) 170, the gripping mechanism 40 being adapted to grip a tooth T of a patient P, the gripping mechanism 40 being slidably positioned between the first elongated member 120 and the second elongated member 130 of the dental bridge 30; a control mechanism 140 (shown most clearly in FIGS. 3A and 3B) positioned inside the housing 20, the control mechanism 140 being configured to control the opening and closing of the gripping mechanism 40 through a sheathed cable 31 (seen in FIG. 4B) housing control wires 155, 156 (seen in FIG. 4A); and a selectively movable member 60 coupled to the housing 20, the selectively moveable member 60 being configured to control the position of the gripping mechanism 40 in relation to the tooth T that is to be extracted, and to rock the tooth after the tooth has been gripped by the gripping mechanism 40 in order to facilitate extraction. As illustrated in FIG. 2, the dental bridge 30 is inserted into the patient's P mouth to support a patient's upper jaw UJ (maxilla) and a patient's lower jaw LJ (mandible), and the opening 35 of the dental bridge 30 is positioned over the tooth T to be extracted to allow the dentist to extract the tooth T by lowering the gripping mechanism 40 onto the tooth T and pulling the tooth T upward in a linear direction.

The housing 20 includes a first portion 25, including a top end 25a, an intermediate portion 26 (seen in FIG. 3A), and a second portion 27 (shown in FIG. 6) coupled to the proximal end 210 of the flexible shaft 200. The second portion 27 of the housing 20 can include at least one link 71 (and preferably a plurality of links 71) to stabilize the second portion 27 of the housing 20. Further, the housing 20 can be configured to include at least two handles, such as handle 22a and handle 22b. The handles 22a, 22b can have any suitable shape, such as circular, configured to receive fingers, such as the index finger and the middle finger of the dentist's hand H to aid the dentist in using the dental extractor 10 to extract the tooth T (FIG. 2) from the patient P.

The housing 20 of the dental extractor 10 can be made from any suitable medical grade material, such as stainless steel, that is capable of being washed and rinsed multiple times to prevent infection and contamination and that is resistant to corrosion. The housing 20 of the dental extractor 10 can have any suitable shape, such as a tubular shape, and can have any suitable length, such as between 15 cm to 20 cm. Further, it is to be appreciated that the housing 20 can be formed from a single, substantially uniform member of suitable material, such as a single piece of stainless steel having a particular length.

Referring to FIG. 2, the top portion 110 of the dental bridge 30, as well as the first bottom support member 120a and the second bottom support member 130a of the dental bridge 30 can have any suitable shape, such as a crescent shape, to protect the teeth in the upper jaw UJ and the teeth in the lower jaw LJ from being damaged during the tooth extraction procedure. It is preferable that the top portion 110 of the dental bridge 30 have a "U" shape and the first bottom support member 120a and the second bottom support member 130a of the dental bridge 30 have an inverted "U" shape so that the dental bridge 30 can be securely held in place by the patient's P teeth. It is to be appreciated that the dentist can insert rubber padding, clay or other type of suitable medical grade material into the U-shaped top portion 110 of the dental bridge 30, as well as into the inverted U-shaped first bottom support member 120a and the second bottom support member 130a to protect the teeth from unnecessary damage and injury from the dental bridge 30 while the tooth extraction procedure is taking place.

The dental bridge 30 of the dental extractor 10 can be made from any suitable medical grade material, such as stainless steel, that is capable of being washed and rinsed multiple times to prevent infection and contamination and that is resistant to corrosion. Further, the dental bridge 30 can have any suitable dimensions, such 3 cm by 4 cm, sufficient to allow the gripping mechanism 40 to be slidably positioned between the first elongated member 120 and the second elongated member 130 and to allow the gripping mechanism 40 to move in an upward and downward direction along the first elongated member 120 and the second elongated member 130 in order to enable the gripping mechanism 40 to move in a downward direction to grab the tooth T, and once it has grabbed the tooth T, to enable the gripping mechanism 40 to move in an upward direction to extract the tooth T.

The gripping mechanism 40, such as a clamp, having the first gripping member 160 and the second gripping member 170 pivotally coupled to the top portion 41, can be made from any suitable medical grade material, such as stainless steel, that is capable of being washed and rinsed multiple times to prevent infection and contamination and that is resistant to corrosion. It is to be appreciated that the first gripping member 160 and the second gripping member 170 can be configured to include serrated edges. It is to be appreciated that the gripping mechanism 40 can be adapted to be substantially aligned with the tooth T to be extracted between the first elongated member 120 and the second elongated member 130 of the dental bridge 30.

The gripping mechanism 40 may also include a connection mechanism 180 having a first connecting member 182 and second connecting member 184, as illustrated FIGS. 4A, 4B, 7A and 7B. The first connecting member 182 and the second connecting member 184 can be attached to one another to secure the gripping mechanism 40 to the wire 70 so that the selectively movable member 60 can be used to move the gripping mechanism 40 in an upward or downward direction along the first elongated member 120 and the second elongated member 130 of the dental bridge 30. It is to be noted that the first connecting member 182 and second connecting member 184 of the connection mechanism 180 can be formed from any suitable medical grade material, such as stainless steel, that is resistant to corrosion and strong enough to hold the gripping mechanism 40.

Figure 3A:
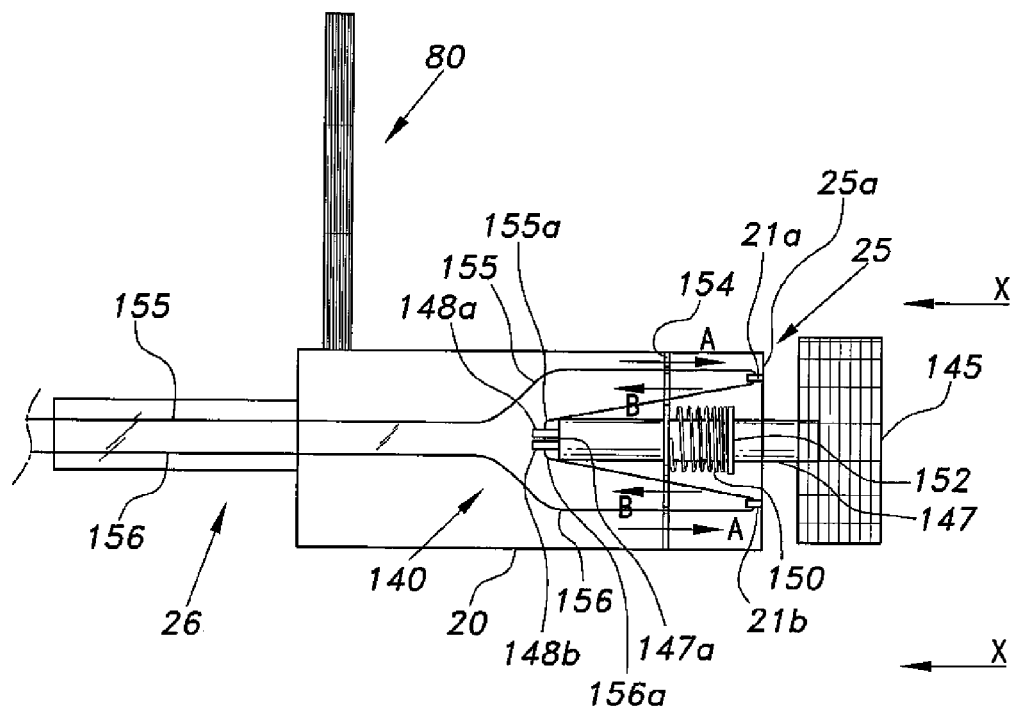
FIG. 3A is a schematic diagram of a control mechanism of the dental extractor of FIG. 1A, illustrating a compressed selectively compressible member and a housing having a coupling member.
Figure 3B:
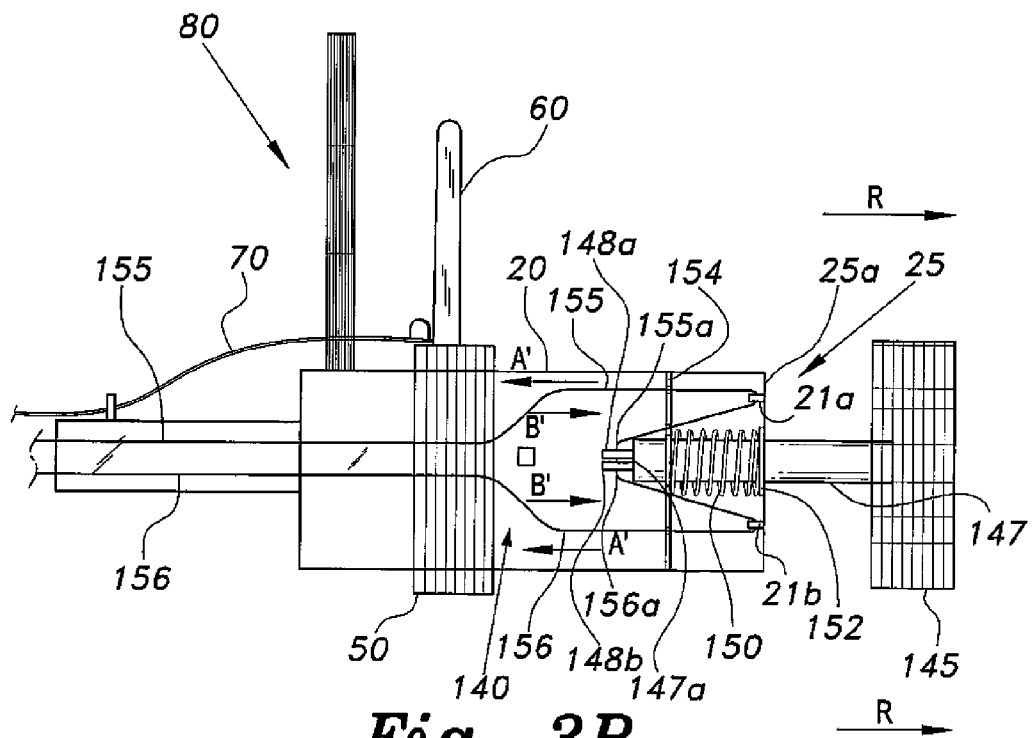
FIG. 3B is a schematic diagram of the control mechanism of FIG. 3A, illustrating an expanded selectively compressible member, and a housing having a coupling member and a selectively movable member.

Referring to FIGS. 3A, 3B, 4A, and 4B, the control mechanism 140 includes a push button 145 having a shaft 147 extending therefrom, the shaft 147 having a tip 147a, at least one and preferably a plurality of control wires, such as a first control wire 155 and a second control wire 156 (which may be housed in a common cable sheath or jacket 31, which is not shown in FIG. 3A to show details of the wires 155, 156) having a fixed length, an annular flange 152 fixed to the shaft 147, a disk 154 (such as a washer) fixed to the inside of the housing 20, the disk 154 having at least one and preferably a plurality of openings adapted to receive the shaft 147 and the control wires 155, 156, a selectively compressible member, such as compression spring 150 (FIGS. 3A, 3B), in communication with the push button 145 (e.g., coiled around the shaft 147 extending from the push button 145), at least one (and preferably a plurality of) guide(s), such as a first guide 21a and a second guide 21b coupled to the inside portion of the top end 25a of the housing 20, and at least one and preferably a plurality of anchors, such as first anchor 148a and second anchor 148b, coupled to the tip 147a of the shaft 147.

The first control wire 155 has a first end 155a and a second end 155b. The first end 155a of the first control wire 155 is coupled to the first anchor 148a positioned at the tip 147a of the shaft 147. The second end 155b of the first control wire 155 is then fed through the first guide 21a of the housing 20 and connected to the top portion 41 of the gripping mechanism 40. Further, the second control wire 156 has a first end 156a and a second end 156b. The first end 156a of the second control wire 156 is coupled to the second anchor 148b positioned at the tip 147a of the shaft 147. The second end 156b of the second control wire 156 is then fed through the second guide 21b of the housing 20 and connected to the top portion 41 of the gripping mechanism 40. It will be understood that the dental extractor 10 can be configured to include a pulley mechanism to control the opening and closing of the first gripping member 160 and the second gripping member 170 of the gripping mechanism 40.

It is to be appreciated that the selectively compressible member, such as compression spring 150, can be formed from any material that is compressible, flexible, and resilient in nature, such as a polymeric or metallic compressible spring, and can be made of any suitable material, such as plastic or metal, that can be compressed when pressure is exerted on the push button 145 and resiliently expands when pressure is relieved from the push button 145. The spring 150 is disposed between the annular flange 152 fixed on the shaft 147 and the disk 154 fixed inside the housing 20, the shaft 147 being slidable through an opening in the disk 154 in the housing 20. When the push button 145 is pressed in, the annular flange 152 compresses the spring 150 against the disk 154 fixed within the housing 20, as illustrated by the arrows X. When the push button 145 is released, the spring 150 expands against the annular flange 152, pushing the push button 145 outward from the housing 20, as illustrated by the arrows R. The control wire, such as the first control wire 155 and the second control wire 156, can be formed from any suitable medical grade material, such as stainless steel, that is resistant to corrosion and has sufficient tensile strength to open and close the gripping mechanism 40.

By way of operation, as illustrated in FIG. 3A, in order to close the first gripping member 160 and the second gripping member 170 of the gripping mechanism 40, the dentist can apply pressure to the push button 145. By applying pressure to the push button 145, as illustrated by arrow X, the first control wire 155 and the second control wire 156 are pulled forward, as illustrated by arrows B, and pulled through the first guide 21a and the second guide 21b, as illustrated by arrows A. The pressure applied to the push button 145, as illustrated by arrow X, also results in the compression of the compression spring 150. This causes the first control wire 155 and the second control wire 156 to tighten and close the first gripping member 160 and the second gripping member 170 of the gripping mechanism 40, which allows the dentist to grab the tooth T that is to be extracted.

In order to release the tooth T after the tooth T has been extracted, the dentist can release the pressure being exerted on the push button 145. By releasing the pressure on the push button 145, the compression on the spring 150 is released, causing the spring 150 to expand and the push button 145 to be pushed out of the housing 20, as illustrated by arrows R in FIG. 3B. This causes the tension of the first control wire 155 and the second control wire 156 to be relaxed, as illustrated by arrows B', and the first control wire 155 and the second control wire 156 to be released through the first guide 21a and the second guide 21b, as illustrated by arrows A'. This causes the first control wire 155 and the second control wire 156 to open the first gripping member 160 and the second gripping member 170 of the gripping mechanism 40, which releases the tooth T that has been extracted.

Figure 4A:
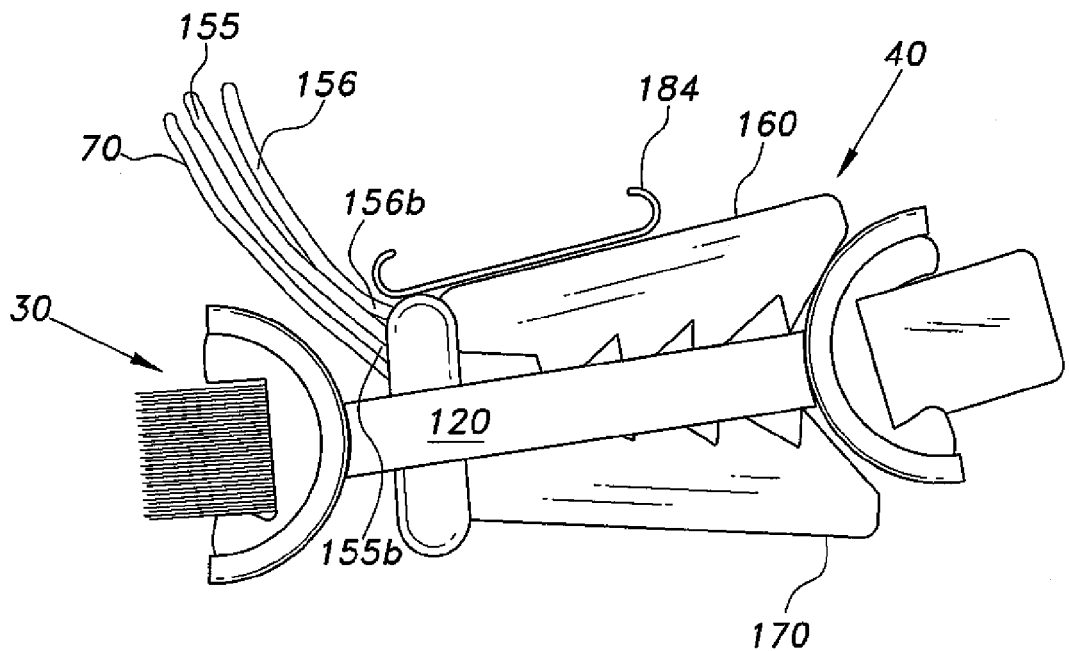
FIG. 4A is side view of a gripping mechanism of the dental extractor of FIG. 1A, showing a second connecting member, the jacket being removed from the sheathed cable to show the control wires.
Figure 4B:
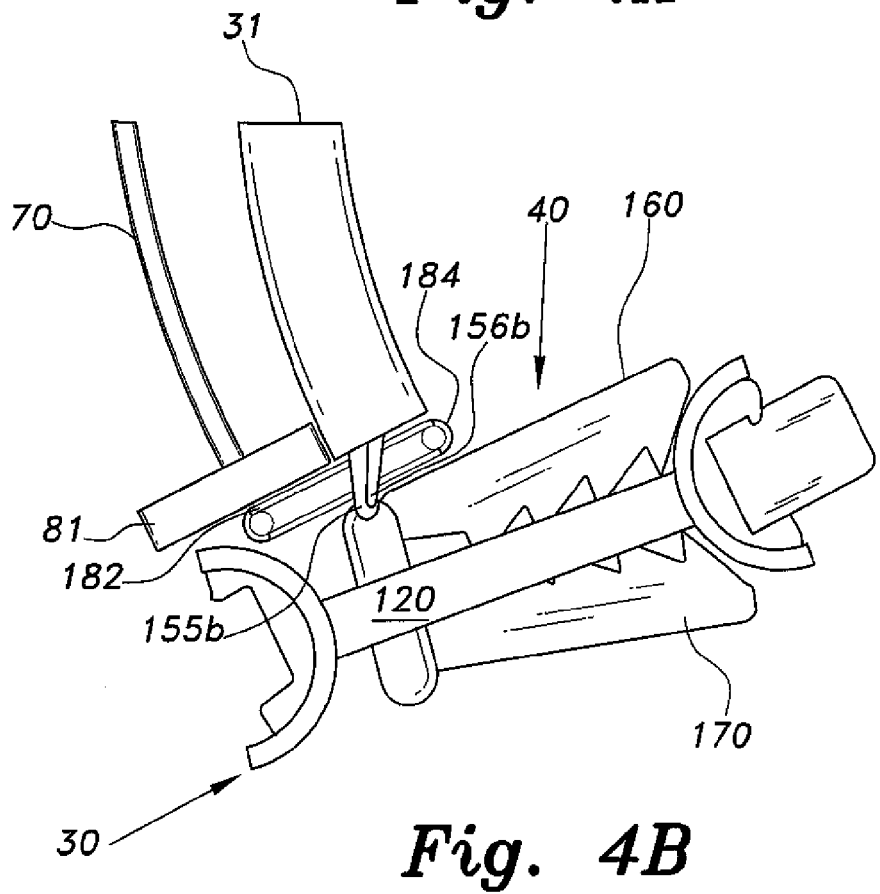
FIG. 4B is a side view of the gripping mechanism of the dental extractor of FIG. 1A, including a connection mechanism having a first connecting member coupled to a second connecting member to secure the gripping mechanism to the dental extractor.

The selectively movable member 60 (lever) can be positioned on a ring member 50 coupled to the housing 20, as illustrated in FIGS. 1A and 1B. The selectively moveable member 60 is attached to a wire 70, the wire 70 being in communication with the gripping mechanism 40, as illustrated in FIGS. 4A and 4B. The wire 70 can include an attachment member 81 to reinforce the connection between the wire 70 and the gripping mechanism 40. The wire 70 can be formed from any suitable medical grade material, such as stainless steel, that is resistant to corrosion and has sufficient tensile strength to hold the dental bridge 30. The wire 70 can extend from the selectively movable member 60 through at least one and preferably a plurality of guides 72 coupled to the housing 20. The selectively movable member 60 can be used to assist the dentist in extracting the tooth T using the gripping mechanism 40, as illustrated by the arrows C & D in FIGS. 1A and 1B. Further, it is to be appreciated that the wire 70 can be positioned inside the lumen of the flexible shaft 200.

Figure 5:
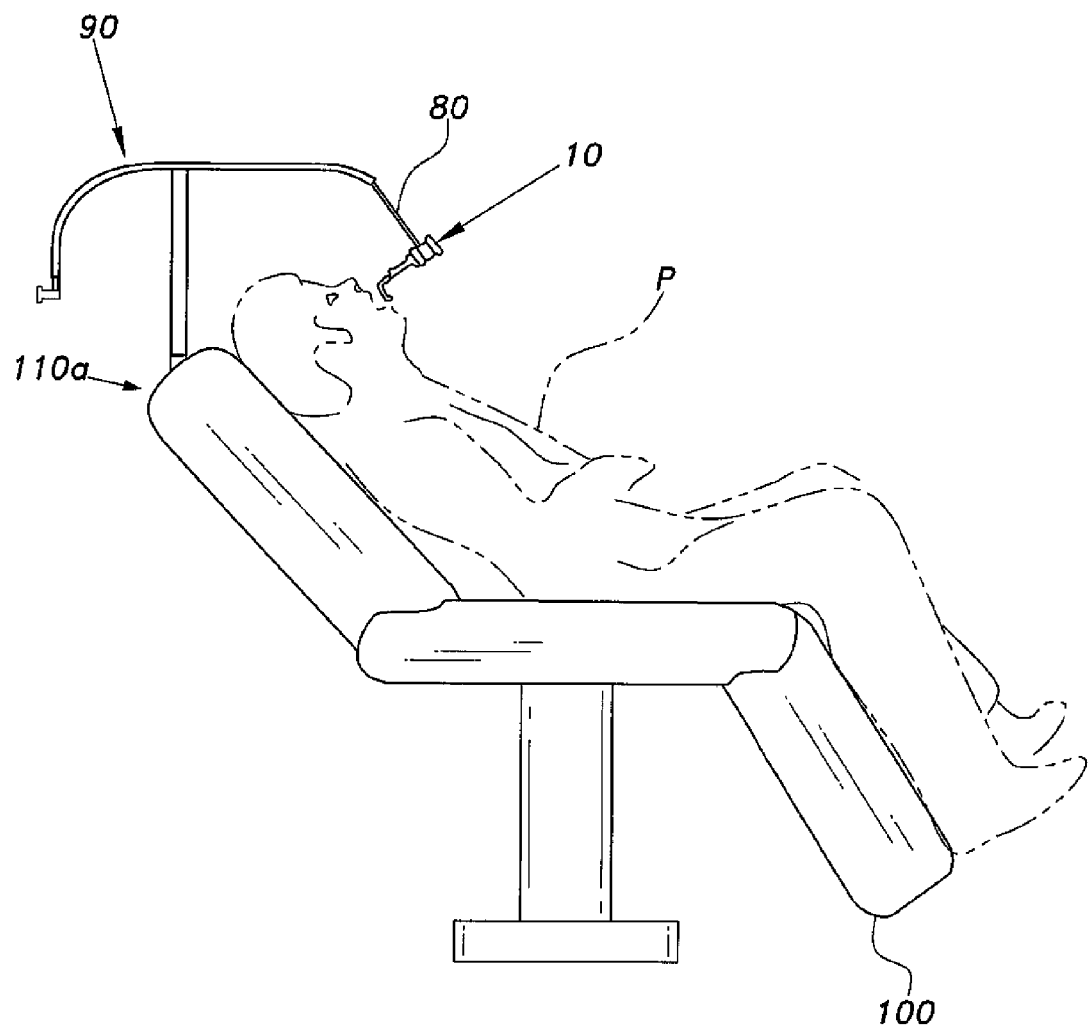
FIG. 5 is an environmental perspective side view of the dental extractor of FIG. 1B, shown coupled to a dental chair.
Figure 6:
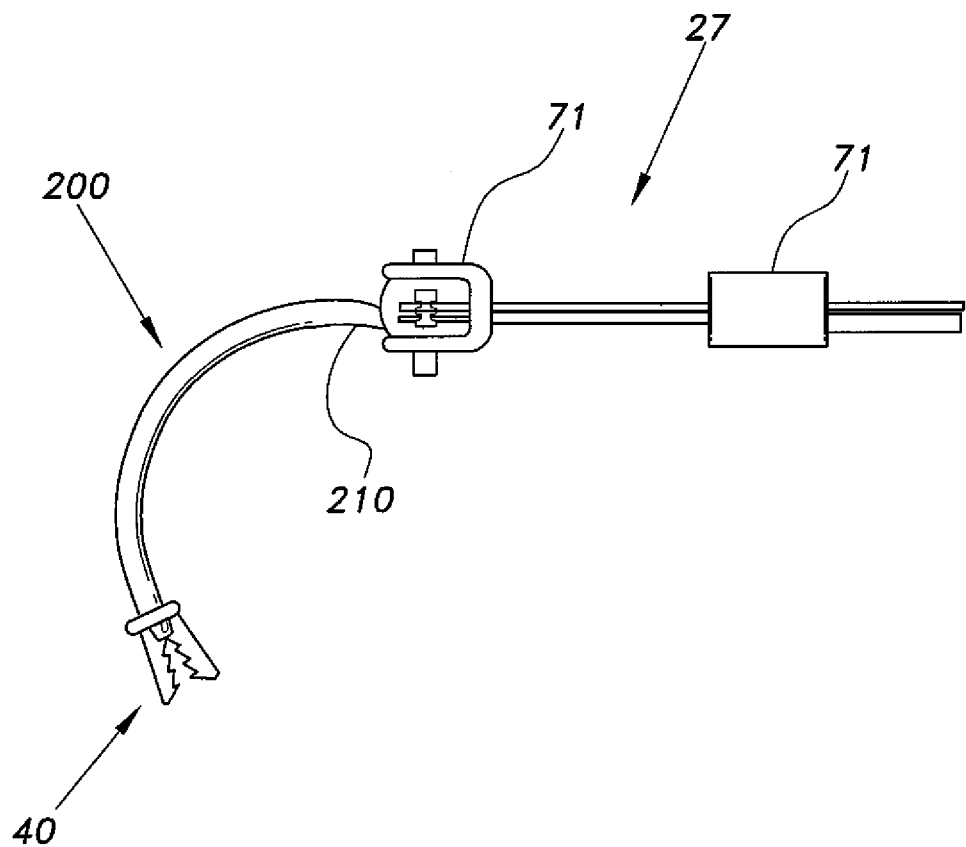
FIG. 6 is a schematic side view of a gripping mechanism of a dental extractor according to the present invention.
Figure 7A:
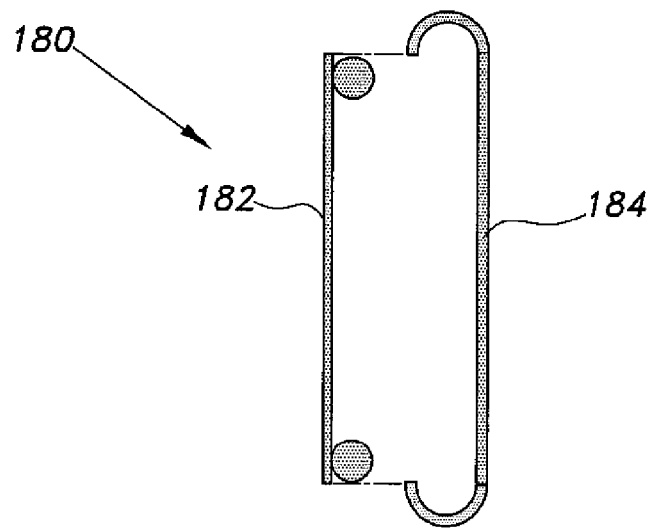
FIG. 7A is a side view in section of a connection mechanism of the dental extractor of FIG. 4B, shown with the first connection member exploded from the second connection member.
Figure 7B:
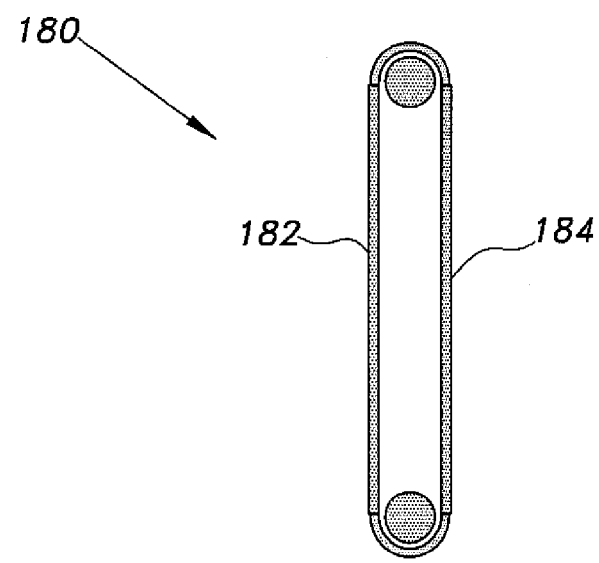
FIG. 7B is a side view in section of the connection mechanism of FIG. 7A, illustrating the first connection member coupled to the second connection member.

Referring to FIGS. 1B and 5, the dental extractor 10 can be configured to include a coupling member 80 coupled to a support member 90 that is configured for attachment onto a dental chair 100, such as on a head portion 100a of a dental chair 100, as illustrated in FIG. 5. The support member 90 can have at least one and preferably a plurality of legs 92, each leg 92 having a proximal end 94 and a distal end 96. Each of the legs 92 has a clamp 98, including a screw 99, positioned at the distal end 96 of each leg 92 to attach the support member 90 onto the head portion 100a of the dental chair 100. It is to be noted that each clamp 98 can be configured to rotate 180° to attach onto the dental chair 100. The support member 90 can be made from any suitable medical grade material, such as aluminum, and can have any suitable shape, such as a crescent shape, to firmly attach onto the dental chair 100 and support the dental extractor 10, as illustrated in FIG. 5.

By way of operation, after the patient P is seated on the dental chair 100, the dentist can attach the dental extractor 10 to the support member 90 using the coupling member 80. The dentist can then position the support member 90 onto the head portion 100a of the dental chair 100 so that the second portion 27 of the housing 20 is pointing towards the inside of the patient's P mouth. Once the support member 90 is positioned over the patient's P head, the screw 99 on each clamp 98 can be tightened so that each leg 92 of the support member 90 is securely fastened onto the head portion 100a of the back rest of the dental chair 100, as illustrated in FIG. 5, to begin the procedure.

After the second end 27 of the dental extractor 10 is pointing towards the inside of the patient's mouth, as illustrated in FIG. 5, the dentist can position the dental bridge 30 in the patient's P mouth with the opening 35 of the dental bridge 30 being positioned on top of the tooth T that is to be extracted, as illustrated in FIG. 2. Once the dental bridge 30 has been properly positioned over the tooth T, the dentist can push the selectively movable member 60 forward, as illustrated by arrows C in FIG. 1A, to let out wire 70 and lower the gripping mechanism 40 along the first elongated member 120 and the second elongated member 130 of the dental bridge 30 onto the tooth T that is to be extracted.

The dentist can then close the gripping mechanism 40 by applying pressure to the push button 145, which causes the control wires, such as the first control wire 155 and the second control wire 156, to tighten and close the first gripping member 160 and the second gripping member 170, respectively; thereby grabbing the tooth T. The dentist can then pull the selectively movable member 60 backward, as illustrated by arrows D in FIG. 1A, to take in the wire 70 and move the gripping mechanism 40 upward along the first elongated member 120 and the second elongated member 130 of the dental bridge 30; thereby extracting the tooth T.

Once the tooth T has been extracted, the dentist can the release the tooth T by relieving the pressure being applied to the push button 145, which causes the control wires, such as the first control wire 155 and the second control wire 156, to relax and open the first gripping member 160 and the second gripping member 170, respectively.

It is to be understood that the present invention is not limited to the embodiments described above, but encompasses any and all embodiments within the scope of the following claims.

I claim:
1. A dental extractor, comprising:
 a housing having a flexible shaft extending therefrom;
 a dental bridge attached to the flexible shaft, the dental bridge having:
 parallel first and second elongated members, each of the first and second elongated members having a first end and a second end;
 a first portion extending across the first ends of the first and second elongated members;

a first support member attached to the second end of the first elongated member; and a second support member attached to the second end of the second elongated member, the first and second support members being spaced apart to define an opening therebetween, the opening in apposition to a tooth selected for extraction;

a gripping mechanism slidably positioned between the first elongated member and the second elongated member of the dental bridge, the gripping mechanism being adapted for gripping the tooth selected for extraction;

a control mechanism positioned inside the housing, the control mechanism being configured to control opening and closing of the gripping mechanism; and a selectively movable member coupled to the housing, the selectively movable member being configured to control position of the gripping member in relation to the tooth selected for extraction.

2. The dental extractor according to claim 1, wherein the housing comprises a tubular housing.

3. The dental extractor according to claim 1, further comprising at least two handles attached to the housing.

4. The dental extractor according to claim 3, wherein the at least two handles comprise two circular rings.

5. The dental extractor according to claim 1, wherein
the gripping mechanism comprises a first gripping member, and a second gripping member, the first and second gripping members being pivotally connected at one end;
wherein the first and second gripping member are selectively disposed between an open position separating the first and second gripping members at a second end opposite the one end, and a closed position urging the second ends of the first and second gripping members towards each other so as to grip the tooth selected for extraction.

6. The dental extractor according to claim 5, wherein the control mechanism comprises:
a push button having a shaft, including a tip;
an annular flange disposed around the shaft of the push button;
a disc fixed inside the housing, the disk having an opening defined therein, the shaft of the push button being slidably disposed in the housing and slidable through the opening in the disk;
a compression spring coaxially disposed on the shaft between the annular flange and the fixed disk, the spring being compressed when the push button is pressed towards the housing, the spring bearing against the annular flange to move the push button away from the housing when the push button is released;
at least one control Wire having a first end attached to the tip of the shaft and a second end attached to the top portion of the gripping mechanism; and
at least one guide coupled to the inside portion of the housing, the at least one control wire having a medial portion passing through the at least one guide;
wherein when the push button is pressed towards the housing, the at least one control wire is pulled forward by the shaft, thereby moving the gripping members to the closed position, and when the push button is released, the spring pushes the push button away from the housing, relaxing tension on the at least one control wire, thereby moving the gripping members to the open position.

7. The dental extractor according to claim 1, further comprising a support member adapted for attachment to a dental chair and a coupling member releasably attaching the support member to the housing.

8. The dental extractor according to claim 7, wherein the support member includes at least one leg adapted to attach onto a dental chair.

9. A dental extractor, comprising:
a housing and a flexible shaft extending from the housing;
a dental bridge attached to the flexible shaft, the dental bridge having:
parallel first and second elongated members, each of the elongated members having a first end and a second end;
a first portion extending across the first ends of the first and second elongated members;
a first support member attached to the second end of the first elongated member; and
a second support member attached to the second end of the second elongated member, the first and second support members being spaced apart to define an opening adapted to receive a tooth selected for extraction between the first and second support members;
a gripping mechanism slidably positioned between the first elongated member and the second elongated member of the dental bridge, the gripping mechanism having a first gripping member, a second gripping member, and a first portion pivotally connecting the first gripping member to the second gripping member, the gripping members being pivotal between an open position separating the gripping members and a closed position urging the gripping members towards each other in order to grip the tooth selected for extraction;
means for controlling pivoting the gripping members between the open position and the closed position;
a lever pivotally attached to the housing;
a wire extending between the lever and the gripping mechanism, the lever selectively rocking the gripping mechanism; and
a support member adapted for attachment to a dental chair and a coupling member releasably attaching the support member to the housing, the support member having at least one leg configured to attach onto a dental chair.

10. The dental extractor according to claim 9, wherein the housing comprises a tubular housing.

11. The dental extractor according to claim 9, wherein the housing comprises at least two handles.

12. The dental extractor according to claim 11, wherein the at least two handles comprise at least two circular rings.

13. The dental extractor according to claim 9, wherein the first gripping member and the second gripping member of the gripping mechanism comprise serrated edges.

14. The dental extractor according to claim 9,
wherein the means for controlling comprises:
a push button having a shaft, including a tip;
an annular flange disposed around the shaft of the push button;
a disc fixed inside the housing, the disk having an opening defined therein, the shaft of the push button being slidably disposed in the housing and slidable through the opening in the disk;
a compression spring coaxially disposed on the shaft between the annular flange and the fixed disk, the spring being compressed when the push button is pressed towards the housing, the spring bearing against the annular flange to move the push button away from the housing when the push button is released;

at least one control wire having a first end attached to the tip of the shaft and a second end attached to the top portion of the gripping mechanism; and at least one guide coupled to the inside portion of the housing, the at least one control wire having a medial portion passing through the at least one guide;

wherein when the push button is pressed towards the housing, the at least one control wire is pulled forward by the shaft, thereby moving the gripping members to the closed position, and when the push button is released, the spring pushes the push button away from the housing, relaxing tension on the at least one control wire, thereby moving the gripping members to the open position.

* * * * *